US009351649B2

(12) United States Patent
Mestha et al.

(10) Patent No.: US 9,351,649 B2
(45) Date of Patent: May 31, 2016

(54) SYSTEM AND METHOD FOR DETERMINING VIDEO-BASED PULSE TRANSIT TIME WITH TIME-SERIES SIGNALS

(71) Applicant: Xerox Corporation, Norwalk, CT (US)

(72) Inventors: Lalit Keshav Mestha, Fairport, NY (US); Survi Kyal, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 121 days.

(21) Appl. No.: 14/026,739

(22) Filed: Sep. 13, 2013

(65) Prior Publication Data

US 2014/0012142 A1 Jan. 9, 2014

Related U.S. Application Data

(63) Continuation-in-part of application No. 13/401,286, filed on Feb. 21, 2012, now Pat. No. 8,838,209.

(51) Int. Cl.
*A61B 5/024* (2006.01)
*A61B 5/00* (2006.01)
(Continued)

(52) U.S. Cl.
CPC .......... *A61B 5/02427* (2013.01); *A61B 5/0075* (2013.01); *A61B 5/02125* (2013.01); *G06T 7/0012* (2013.01); *G06T 2207/30076* (2013.01); *G06T 2207/30104* (2013.01)

(58) Field of Classification Search
CPC .................. G06T 2207/30104; G06T 7/0012; A61B 5/0075; A61B 5/02125
See application file for complete search history.

(56) References Cited

U.S. PATENT DOCUMENTS 5,062,703 A * 11/1991 Wong et al. ................... 356/73.1
5,241,964 A * 9/1993 McQuilkin ........ A61B 5/02125
600/485
(Continued)

FOREIGN PATENT DOCUMENTS

PL    EP 1489391 A2 * 12/2004 ............... G01F 1/66
WO   WO2012007423 A1    1/2012
OTHER PUBLICATIONS

M. Lewandowska, J. Ruminski, T. Kocejko, J. Nowak, "Meauring Pulse Rate with a Webcam—A Non-contact Method for Evaluating Cardiac Activity", Proceedings of the Federated COnference on COmputer Science and Information Systems, pp. 405-410, 2011.*
(Continued)

*Primary Examiner* — Tse Chen
*Assistant Examiner* — Joanne Hoffman
(74) *Attorney, Agent, or Firm* — Philip E. Blair; Fleit Gibbons Gutman Bongini & Bianco P.L.

(57) ABSTRACT

What is disclosed is a system and method for determining a subject of interest's arterial pulse transit time from time-varying source signals generated from video images. In one embodiment, a video imaging system is used to capture a time-varying source signal of a proximal and distal region of a subject of interest. The image frames are processed to isolate localized areas of a proximal and distal region of exposed skin of the subject. A time-series signal for each of the proximal and distal regions is extracted from the source video images. A phase angle is computed with respect to frequency for each of the time-series signals to produce respective phase v/s frequency curves for each region. Slopes within a selected cardiac frequency range are extracted from each of the phase curves and a difference is computed between the two slopes to obtain an arterial pulse transit time for the subject.

26 Claims, 5 Drawing Sheets

(51) Int. Cl.
*A61B 5/021* (2006.01)
*G06T 7/00* (2006.01)

(56) References Cited

U.S. PATENT DOCUMENTS

| | | | |
|---|---|---|---|
| 6,405,132 B1* | 6/2002 | Breed et al. | 701/301 |
| 6,587,701 B1* | 7/2003 | Stranc et al. | 600/310 |
| 7,558,618 B1* | 7/2009 | Williams | A61B 5/0059 600/407 |
| 7,728,868 B2* | 6/2010 | Razzaque et al. | 348/77 |
| 8,313,439 B2 | 11/2012 | McCombie et al. | |
| 2003/0060696 A1* | 3/2003 | Skladnev et al. | 600/409 |
| 2004/0215072 A1* | 10/2004 | Zhu | 600/407 |
| 2006/0291849 A1* | 12/2006 | Shamir et al. | 396/334 |
| 2008/0045847 A1* | 2/2008 | Farag et al. | 600/500 |
| 2008/0081994 A1* | 4/2008 | Kim | A61B 5/0285 600/438 |
| 2010/0204592 A1* | 8/2010 | Hatib | A61B 5/02028 600/485 |
| 2012/0147194 A1 | 6/2012 | Wang et al. | |
| 2012/0200682 A1 | 8/2012 | Mestha et al. | |
| 2012/0262577 A1 | 10/2012 | Wang et al. | |
| 2013/0079649 A1 | 3/2013 | Mestha et al. | |
| 2013/0108236 A1 | 5/2013 | Mestha et al. | |
| 2013/0148847 A1 | 6/2013 | Wang et al. | |
| 2013/0215244 A1 | 8/2013 | Mestha et al. | |

OTHER PUBLICATIONS

European Search Report, dated Jun. 12, 2013, for EP 13 15 5181.
Allen, John, "Photoplethysmography and its application in clinical physiological measurement", Physiological Measurement, vol. 28, No. 3, Mar. 1, 2007, pp. R1-R39.
Kalsi, Mastan Singh, "Design of Arterial Blood Pressure, Heart Rate Variability, and Breathing Rate Monitoring Device", Electrical and Biomedical Engineering Design Project, Apr. 23, 2009, pp. 1-65.
Norris, Suzette, "Innovation Conversation: What Some Xerox Researches Do on their Lunch Hour", Xerox Newsroom News & Features, Feb. 8, 2013.
Pressman et al., "A Transducer for the Continuous External Measurement of Arterial Blood Pressure", External Measurement of Blood Pressure, IEEE Transactions on Bio-Medical Electronics, Apr. 1963, pp. 73-81.
Meigas, et al., "Continuous Blood Pressure Monitoring Using Pulse Wave Delay", Proposed Paper; Engineering in Medicine and Biology Society, 2001, vol. 4, pp. 3171-3174, Proceedings of the 23rd Annual Int'l Conf. of the IEEE.
Penaz, J., "Photoelectric Measurement of Blood Pressure, Volume and Flow in the Finger", Dresden, 10th Int. Conf. Med. and Biol. Engineering, 1973, Session 7, N2, Haemodynamics I, pp. 161-164.
Aubert et al., "A Model-Based Study of the Influence of Vaso-Active Drugs on Pulse Delays Measured from the Electrocardiogram", Computers in Cardiology 2007:34:383-386.
Naschitz et al., "Pulse Transit Time by R-Wave-Gated Infrared Photoplethysmography: Review of the Literature and Personal Experience", Journal of Clinical Monitoring and Computing (2004) 18: 333-342, Springer 2005.
Reisner et al., "Utility of the Photoplethysmogram in Circulatory Monitoring", Anesthesiology, vol. 108, No. 5, May 2008, pp. 950-958.
Gao et al., "Perturbationless Calibration of Pulse Transit Time to Blood Pressure", 34th Annual International Conference of the IEEE EMBS, California USA, Aug. 2012, pp. 232-235.
Sahoo et al., "Wavelet Based Pulse Rate and Blood Pressure Estimation System From ECG and PPC Signals", International Conference on Computer, Communication and Electrical Technology, Mar. 2011, pp. 285-289.
Ye et al., "Estimation of Systolic and Diastolic Pressure using the Pulse Transit Time", World Academy of Science, Engineering and Technology 43, May 2010, pp. 726-731.
Yoshizawa, et al, "A Great Impact of Green Video Signals on Tele-Healthcare in Daily Life, Especially for Rural or Disaster Areas", 35th Annual International Conference of the IEEE EMBS Osaka, Japan, Jul. 3-7, 2013.

* cited by examiner

SYSTEM AND METHOD FOR DETERMINING VIDEO-BASED PULSE TRANSIT TIME WITH TIME-SERIES SIGNALS

CROSS REFERENCE TO RELATED APPLICATIONS

This patent application is a continuation-in-part to commonly owned and co-pending U.S. Pat. No. 8,838,209, "Deriving Arterial Pulse Transit Time From A Source Video Image", by Mestha.

TECHNICAL FIELD

The present invention is directed to systems and methods for determining the patient's arterial pulse transit time from a source video signal acquired of that patient.

BACKGROUND

The ability to capture physiological signals by non-contact means is highly desirable in the healthcare industry. One physiological signal of importance is the pulse transit time for many reasons, one of which is that the pulse transit time has a correlation with blood pressure. To obtain such measurements, electrodes of an electro-cardiogram (ECG) device need to be attached directly to the patient's skin. This can be a problem in neonatal intensive care units caring for premature babies with sensitive skin.

Accordingly, what is needed in this art are systems and methods for determining a subject of interest's arterial pulse transit time from time-varying source signals generated from video images.

INCORPORATED REFERENCES

The following U.S. Patents, U.S. Patent Applications, and Publications are incorporated herein in their entirety by reference.

"Estimating Cardiac Pulse Recovery From Multi-Channel Source Data Via Constrained Source Separation", U.S. Pat. No. 8,617,081, by Mestha et al.

"Filtering Source Video Data Via Independent Component Selection", U.S. Pat. No. 8,600,213, by Mestha et al.

"Method For Classifying A Pixel Of A Hyperspectral Image In A Remote Sensing Application", U.S. Pat. No. 9,019,358, by Mestha et al.

"Determining A Total Number Of People In An IR Image Obtained Via An IR Imaging System", U.S. Pat. No. 8,520,074, application Ser. No. 12/967,775, by Wang et al, which discloses a ratio method for classifying pixels in an IR image.

"Determining A Number Of Objects In An IR Image", U.S. Pat. No. 8,587,657, by Wang et al, which discloses a correlation method and a best fitting reflectance method for classifying pixels in an IR image.

"Post-Processing A Multi-Spectral Image For Enhanced Object Identification", U.S. Pat. No. 8,818,030, by Wang et al.

"Removing Environment Factors From Signals Generated From Video Images Captured For Biomedical Measurements", U.S. patent application Ser. No. 13/401,207, by Mestha et al.

BRIEF SUMMARY

What is disclosed is a system and method for determining a subject of interest's arterial pulse transit time from time-varying source signals generated from video images. In one embodiment, a video imaging system is used to capture a time-varying source signal of a proximal and distal region of a subject of interest. The image frames are processed to isolate localized areas of a proximal and distal region of exposed skin of the subject. A time-series signal for each of the proximal and distal regions is extracted from the source video. A phase angle is computed with respect to frequency for each of the time-series signals to produce respective phase v/s frequency curves for each region. Slopes within a selected cardiac frequency range are then extracted from each of the phase v/s frequency curves. A difference is computed between the two slopes to obtain an arterial pulse transit time for the subject.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for determining a subject of interest's arterial pulse transit time from time-varying source signals generated from video images.

NON-LIMITING DEFINITIONS

A "subject of interest", as used herein, refers to any subject which is capable of registering an arterial pulse. The present method applies equally to any subjects capable of registering an arterial pulse. Use of terms herein for explanatory purpose, such as "person" or "patient", are not to be viewed as limiting the scope of the appended claims solely to human subjects.

"Proximal" (from the Latin proximus: meaning nearest to) refers to a point that is nearer to the source of the arterial pulse which is in the ascending aorta. Note that the systemic arterial system originate from the aorta. As left ventricle of the heart contracts blood exits from the ascending aorta in the form of waves and flows into systemic arteries. The heart is located near the anterior chest wall, directly posterior to the sternum.

For arterial pulse measurement, a proximal point in an artery is a point which is closer to the heart, i.e., upstream from the distal point.

"Distal" (from the Latin distare: meaning away from) refers to a point that is farther from a center of the body. For arterial pulse measurement purposes, the distal point in the artery is a point which is farther from the heart, i.e., upstream or downstream from the proximal point as the arterial network carries blood upstream & downstream through the branches of the aortic arch and the descending aorta. By drawing an imaginary line between the proximal and distal points, a proximo-distal axis is created. The elbow is proximal to the wrist but distal to the shoulder since the blood flows from brachial arteries towards the wrist through radial and ulnar arteries. Blood vessels may also be labeled as "ostial" (referring to point where the blood vessel branches off) and "distal" (referring to a point away from the branch point).

An "arterial pulse wave" is a pressure wave created throughout the vascular system when the left ventricle of the heart muscle contracts and pushes a volume of blood into the aorta. This generates a perturbation that travels from the heart and down into the arterial network. An arterial pulse wave has two primary components, i.e., a forward traveling wave when the left ventricle contracts, and a reflected wave returning back from the peripheral. The actual pressure in the aorta is the sum of the initial wave and the reflected wave.

Figure 1:
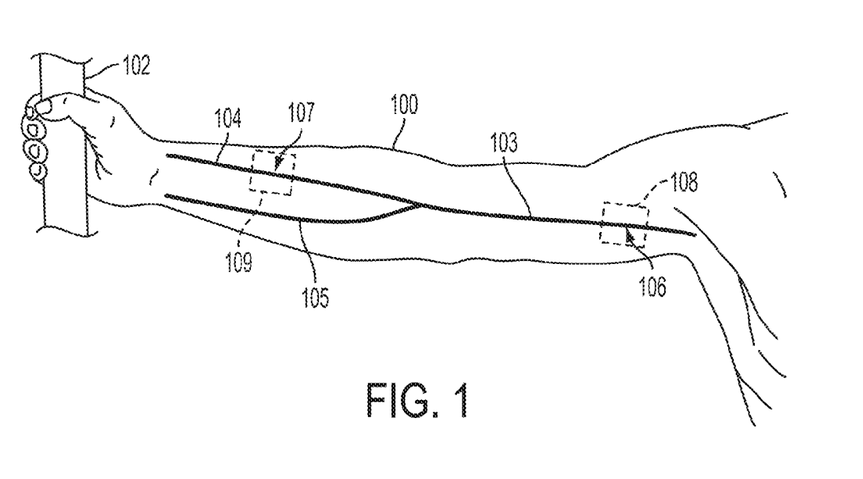
FIG. 1 shows a subject of interest's right arm extremity clutching a pole to illustrate two proximal and distal points in the arterial system of the human arm.

The "pulse transit time" refers to the time it takes a pressure pulse to travel from a proximal arterial site to a distal arterial site. Pulse transit time (PTT) is a function of the pulse wave velocity which, in turn, is a function of the blood pressure, vessel diameter, blood density. Localized PTT is used as an indirect marker of various pathologic conditions. PTT has high correlations when utilized as a surrogate monitor of BP changes. Present literature suggests that description of disease-specific cardiovascular reactivity pattern is feasible with techniques that are based upon PTT. PTT signals can be calibrated to extract beat-to-beat blood pressure and blood velocity in the patient's vascular network including facilitating for variety of diagnosis such as, for example, blood vessel dilation over time, vessel blockage between two points (or regions) of interest, peripheral neuropathy for diabetic patients etc. FIG. 1 shows a subject of interest's right arm 100 extended outward and clutching a section of a pole 102. The subject's brachial artery 103 extends down the arm and branches into the radial and ulnar arteries, at 104 and 105 respectively. A point 106 in the brachial artery is proximal to a point 107 in the radial artery. In FIG. 1 and for discussion purposes, the pulse transit time is the time it takes for the arterial pulse wave to travel from point 106 in proximal region 108 to point 107 in distal region 109. When face and hand regions are selected, since there is no vascular network directly connecting between face and the hand, the video-based pulse transit time takes the meaning of time difference between face signal and hand signal.

"Source video images" are a time-varying sequence of images acquired using a video imaging sensor. A source video image can be any combination of: NIR images, RGB images, RGB with NIR images, thermal, multi-spectral images, and hyperspectral video images. It should be appreciated that when the video capture is made in the NIR band, enough illumination will be required to image in the infrared wavelength.

A "video imaging sensor" refers to a device for acquiring source video data over one or more channels. The video imaging sensor may be a device with a high frame rate and high spatial resolution such as, for example, a monochrome camera for capturing black/white video images, or a color camera for capturing color video images. The video imaging sensor may be a spectral sensor such as a thermal, multi-spectral or hyperspectral system. The imaging sensor may be a hybrid device capable of operating in a conventional video mode with high frame rates and high spatial resolution, and a spectral mode with low frame rates but high spectral resolution. Video imaging sensors comprising standard video cameras and those comprising specialized sensors are readily available from a wide array of vendors in various streams of commerce.

A "remote sensing environment" refers to non-contact, non-invasive sensing, i.e., the imaging sensor does not physically contact the subject being sensed. The environment may be any settings such as, for example, a hospital, ambulance, medical office, and the like.

Example Flow Diagram of One Embodiment

Figure 2:
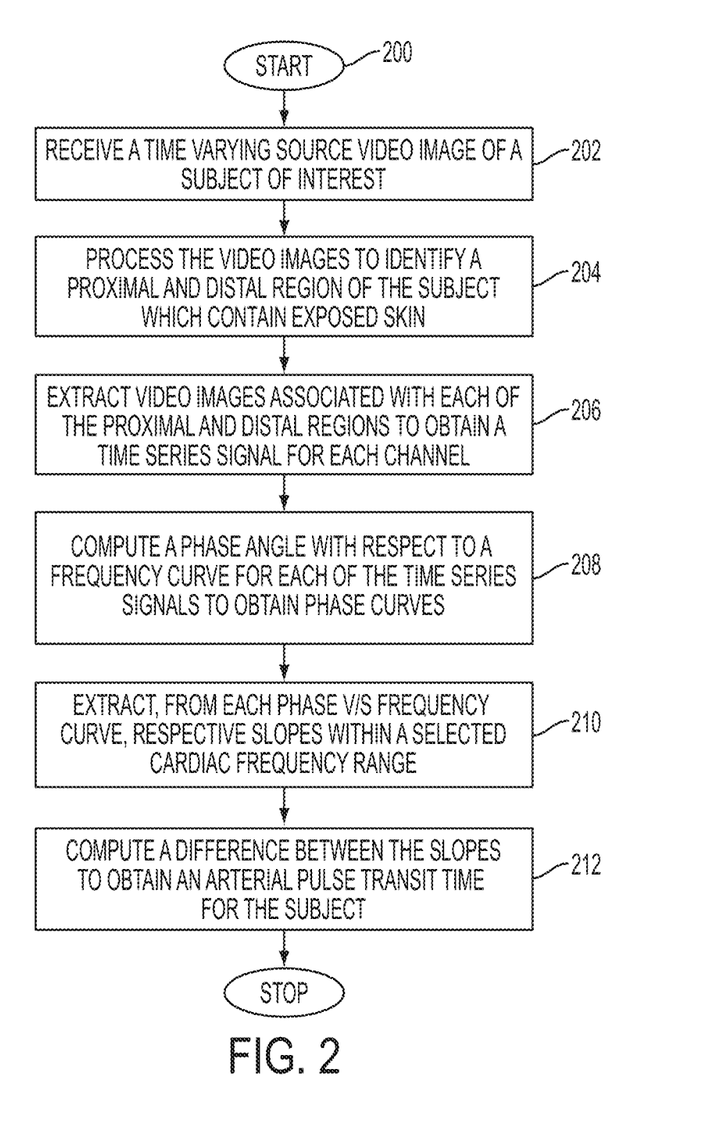
FIG. 2 is a flow diagram which illustrates one embodiment of the present method for determining an arterial pulse transit time between a proximal and distal region of a subject of interest from source video images acquired using a video imaging system.

Reference is now being made to the flow diagram of FIG. 2 which illustrates one embodiment of the present method for determining an arterial pulse transit time between a proximal and distal region of a subject of interest from source video images acquired using a video imaging system. Flow processing begins at step 200 and immediately proceeds to step 202.

At step 202, a time-varying source images is received which has been captured of a subject of interest. The source video images have been acquired over at least one channel of a video imaging system. The source images comprise a plurality of image frames.

At step 204, the video images are processed to identify a proximal and a distal region of the subject which contain areas of exposed skin. Example proximal and distal regions are shown and described with respect to regions 108 and 109 of FIG. 1, respectively. Areas of exposed skin can be determined in an image by analyzing the video images, on a frame-by-frame basis, and classifying the pixels comprising in those image frames. Pixels classified as human skin can be identified using, for example, the above-incorporated pixel classification methods.

At step 206, video images associated with each of the identified proximal and distal regions are extracted from the source images to obtain a time-series signal for each channel. The signal corresponds to volumetric changes in blood pressure. This can be effectuated by computing an average of all pixels in each of the identified proximal and distal regions within each image frame to obtain a channel average per frame for each of the regions. A global channel average can then be computed, for each channel, by adding the channel averages across multiple frames and dividing by the total number of frames. The channel average is subtracted from the global channel average and the result is divided by a global channel standard deviation to obtain a zero-mean unit variance time-series signal for each of the proximal and distal regions. These time-series signals contain frequency components. For the purpose of determining the pulse transit time, processing with only a single color channel is adequate. For example, in a RGB video, time-series signals from the green channel contain a sufficient signal. Once normalized time-series signals have been obtained for each of the proximal and distal regions, these are then subjected to a pre-filtering to remove undesirable frequencies using a Fast Fourier Transform (FFT) algorithm. The resulting pre-processed and pre-filtered time-series signals contain the sum total of volumetric pressure changes within each region. Further pre-processing can be done to extract the source blood volume signals (such as the plethysmographic signals) using blind source separation algorithms such as the independent component analysis or the constrained independent component analysis as described in the aforementioned references. It should be understood that the volume changes in the first and second regions are due to all the blood vessels in each of those regions. Arterial pulsations are a dominant component in these signals. Components from smaller structures such as capillaries and terminal arterioles although are less significant as these only provide a minor contribution to the registered pulsations, but may be significant when the region of interest is large as the integrated effect may improve signal to noise ratio. If camera related noise or other environmental factors affecting the video capture are present, compensation can be introduced as described in the above-incorporated reference entitled: "Removing Environment Factors From Signals Generated From Video Images Captured For Biomedical Measurements", By Mestha et al. The post-compensated signal contains decorrelated and noise corrected channels, i.e., environmentally compensated signals for each of the proximal and distal regions.

At step 208, compute a phase angle with respect to frequency for each of the time-series signals to obtain respective phase v/s frequency curves of frequencies within these signals. Only one of the video channels can be used to determine the phase v/s frequency curves. If a source separation algorithm is used then the source signals from proximal and distal regions will be used to compute the phase v/s frequency curves. One of ordinary skill will readily understand how to compute a phase angle 1 (1) with respect to frequency 1 given a time-series signal. If $1_1(1)$ is the phase of the time-series signal corresponding to the proximal region and $1_1(1)$ is the phase of the time-series signal corresponding to the distal region then $1_1 = {}^{111}1_{11}$ and $1_1 = {}^{111}1_{11}$ are respective slopes. These slopes may be computed by fitting a polynomial equation to each of the phase v/s frequency curves or by taking derivative with respect to frequency. If the phase with respect to frequency curve is linear then all the frequencies contained within the time-series signal have same time shift.

At step 210, extract, from each phase v/s frequency curves, respective slopes within a selected cardiac frequency range. One cardiac frequency range is 0.75 to 4.0 Hz. Slopes represent time shift of each harmonics within the respective time-series signal.

Figure 3:
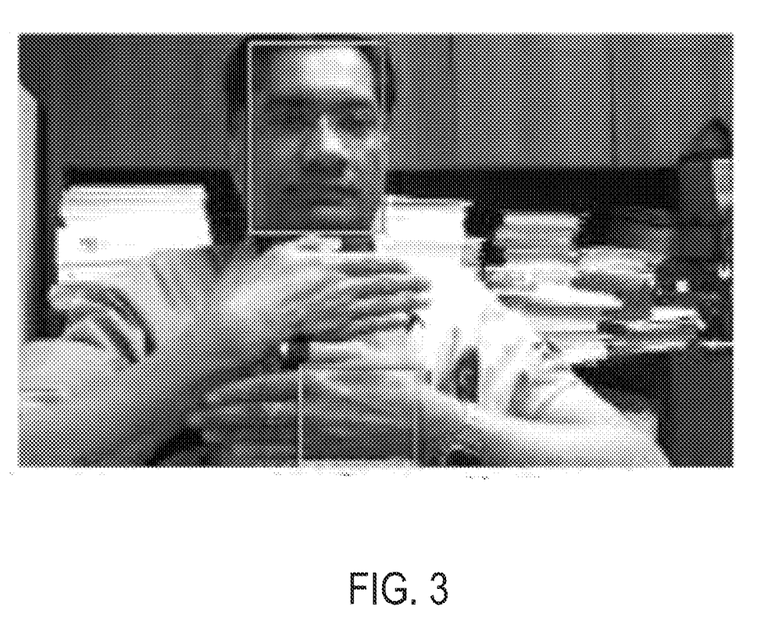
FIG. 3 is an image of a subject with a proximal region identified as being a region of the back of the hand and a distal region identified as being a region of the face.
Figure 4:
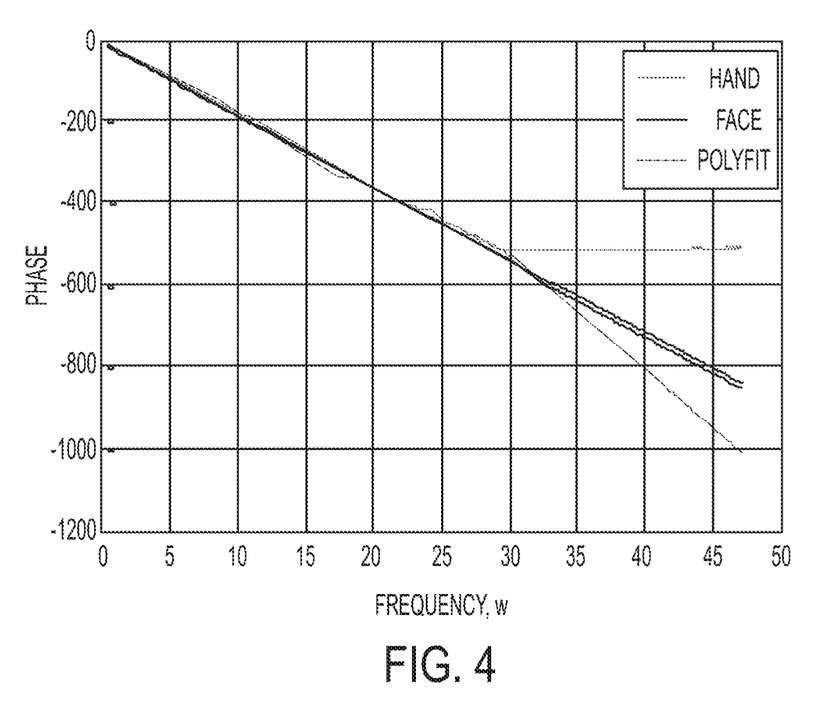
FIG. 4 shows the plotted slopes for the phase angle with respect to frequency curves obtained from having processed the time-varying source signals for each of the proximal and distal regions of FIG. 3, in accordance with the teachings hereof.

At step 212, compute a difference between the slopes to obtain an arterial pulse transit time for the subject. In this embodiment, further processing stops. FIG. 3 shows an image of a subject with a distal region identified as being a region of the back of the hand and a proximal region identified as being a region of the subject's face. FIG. 4 shows the plotted phase v/s frequency curves with respect to frequency obtained for each of the proximal and distal regions of FIG. 3. These phase v/s frequency curves exhibit linear characteristics with respect to frequency within the cardiac frequency range. The slope of the hand region is −18.0917 seconds. The slope of the facial region is −17.5271 seconds. The computed difference corresponding to the subject's arterial pulse transit time between the proximal and distal regions is 0.5647 sec. The slope difference of the two linear phase v/s frequency curves corresponds to the propagation (or time) delay for the blood to flow between these two regions. It is to be noted that the phase v/s frequency curves may not be linear in all subjects of varying levels of disease state.

In other embodiments, the arterial pulse transit time is communicated to a computer system and used to facilitate a determination of any of: a blood pressure in the subject's vascular network, a blood vessel dilation over time, a blood vessel blockage, a blood flow velocity, and/or the existence of a peripheral neuropathy.

It should be appreciated that the flow diagrams hereof are illustrative. One or more of the operative steps illustrated in the flow diagram may be performed in a differing order. Other operations, for example, may be added, modified, enhanced, condensed, integrated, or consolidated. Such variations are intended to fall within the scope of the appended claims. All or portions of the flow diagrams may be implemented partially or fully in hardware in conjunction with machine executable instructions.

Source Signal Processing System

Figure 5:
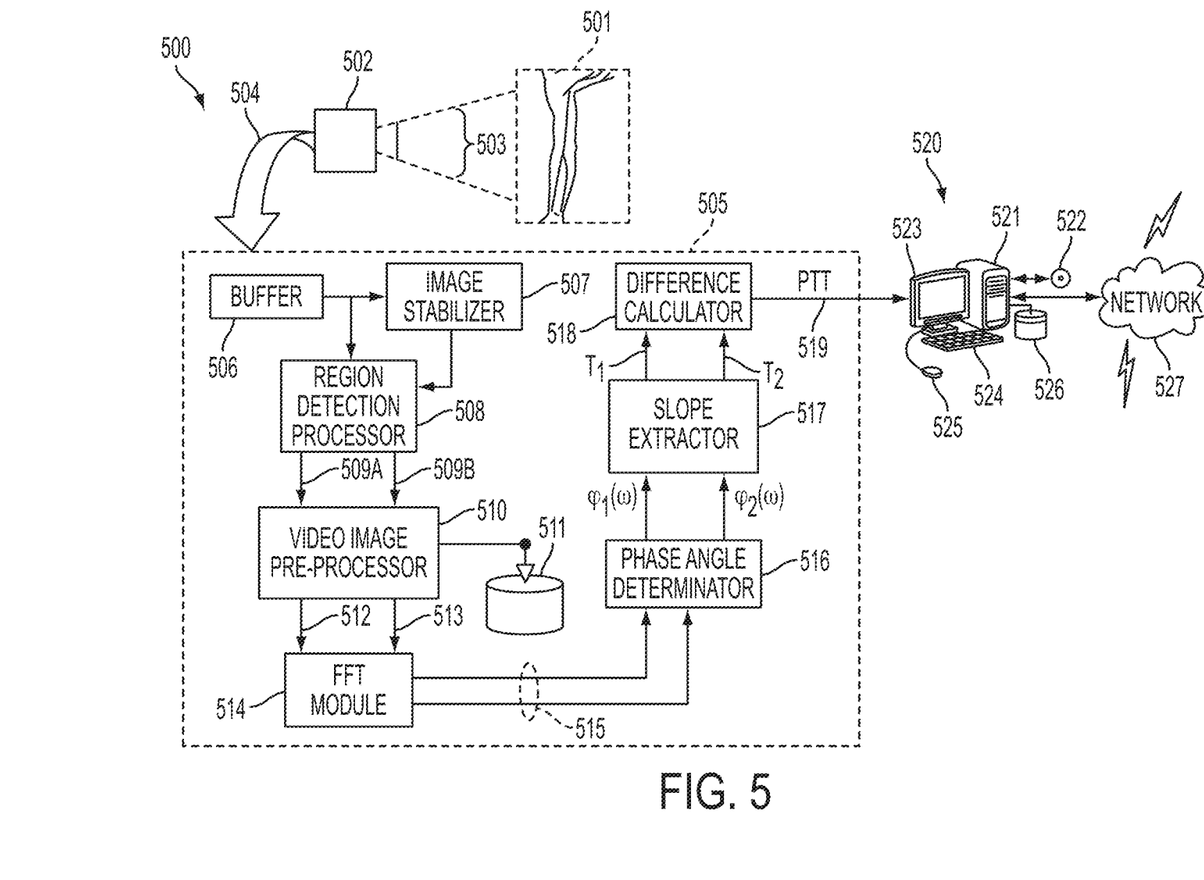
FIG. 5 is a block diagram of an example networked image processing system wherein various aspects of the present method, as described in the flow diagram of FIG. 2, are implemented.

Reference is now being made to FIG. 5 which is a block diagram of an example networked video image processing system 500 wherein various aspects of the present method as described with respect to the flow diagram of FIG. 2 are implemented.

In FIG. 5, imaging sensor 502 acquires source video images 501 of a subject of interest (shown as a right arm) captured in the video camera's field of view 503. The source video images are acquired over at least one imaging channel and the signals 504 for each channel are communicated to Video Image Processing System 505 wherein various aspects of the present method are performed.

System 505 is shown comprising a Buffer 506 for buffering the source signal for processing. Buffer 506 may further store data, formulas, mathematical representations, and the like, as are needed to process the source video images in accordance with the teachings hereof. Image Stabilizer Module 507 processes the images to compensate, where needed, for anomalies such as motion induced blur, imaging blur, slow illuminant variation, and the like. Region Detection Processor 508 receives the video images and processes the images contained therein in order to determine a proximal and a distal region, at 509A and 509B, respectively. One or more frames of the captured source video image may be communicated by pathways not shown to workstation 520 for display 523 thereon such that the user can select any of the proximal and distal regions from any of the captured image frames. A selection may be made by the user using, for example, a rubber-band box created by clicking and dragging a mouse or by otherwise highlighting localized areas of exposed skin in one or more image frames of the video sequence for processing.

Portions of the source images associated with each of the proximal and distal regions are provided to Video Image Pre-Processor 510 which receives the source images associated with each of the identified proximal and distal regions and extracts a time-series signal from the source images for each channel of each region. Various signal components may be stored/retrieved to storage device 511 using communication pathways not shown. The normalized time-series signals 512 and 513, extracted for the proximal and distal regions respectively, are provided to FFT Module 514 wherein these time-series signals are subjected to a pre-filtering to remove undesirable frequencies. FFT Module may also use other filtering techniques. The filtered time-series signals, collectively at 515, are provided to Phase Angle Determinator 516 which receives the filtered time-series signals for each of the proximal and distal regions and computes a phase 1 with respect to frequency for each of the time-series signals for a selected channel of interest to obtain phase v/s frequency curves. Slope Extractor 517 receives the phase v/s frequency curves for the proximal and distal regions, $1_1(1)$ and $1_1(1)$, respectively, and extracts, from each of the phase v/s frequency curves, slopes ($T_1$ and $T_2$) within a selected cardiac frequency range. Difference Calculator 518 computes a difference between the two slopes to obtain an arterial pulse transit time (PTT) 519 for the subject. The arterial pulse transit time is communicated to networked computer system 520.

Workstation 520 reads/writes to computer readable media 522 such as a floppy disk, optical disk, CD-ROM, DVD, magnetic tape, etc. Case 521 houses a motherboard with a processor and memory, a network card, graphics card, and the like, and other software and hardware. The workstation includes a user interface which, in this embodiment, comprises display 523 such as a CRT, LCD, touch screen, etc., a keyboard 524 and a mouse 525. A user or technician may use the keyboard and/or mouse to identify the proximal and distal regions, set parameters, select images for processing, view results, and the like. It should be appreciated that the workstation has an operating system and other specialized software configured to display a variety of numeric values, text, scroll bars, pull-down menus with user selectable options, and the like, for entering, selecting, or modifying information displayed on display device 523. Various portions of the source video signals captured by video capture device 502 may be communicated to workstation 520 for processing and stored to storage device 526. Workstation 520 is in communication with one or more remote devices of network 527 via a communications interface internal to case 521.

It should be appreciated that some or all of the functionality performed by any of the modules and processing units of the signal processing system 505 can be performed, in whole or in part, by workstation 520. Any of these may be stored to storage device 526 or written to computer media 522. Any of the modules and processing units of FIG. 5 can be placed in communication with storage devices 511 and 526 and may store/retrieve therefrom data, variables, records, parameters, functions, machine readable/executable program instructions required to perform their intended functions. Each of the modules of system 505 may be placed in communication with one or more devices over network 527. Although shown as a desktop computer, it should be appreciated that computer system 520 can be any of a laptop, mainframe, server, or a special purpose computer such as an ASIC, circuit board, dedicated processor, or the like.

It should also be appreciated that various modules may designate one or more components which may, in turn, comprise software and/or hardware designed to perform the intended function. A plurality of modules may collectively perform a single function. Each module may have a specialized processor capable of executing machine readable program instructions. A module may comprise a single piece of hardware such as an ASIC, electronic circuit, or special purpose processor. A plurality of modules may be executed by either a single special purpose computer system or a plurality of special purpose computer systems operating in parallel. Connections between modules include both physical and logical connections. Modules may further include one or more software/hardware modules which may further comprise an operating system, drivers, device controllers, and other apparatuses some or all of which may be connected via a network. It is also contemplated that one or more aspects of the present method may be implemented on a dedicated computer system and may also be practiced in distributed computing environments where tasks are performed by remote devices that are linked through a network. The teachings hereof can be implemented in hardware or software using any known or later developed systems, structures, devices, and/or software by those skilled in the applicable art without undue experimentation from the functional description provided herein with a general knowledge of the relevant arts.

Various Embodiments

One or more aspects of the methods described herein are intended to be incorporated in an article of manufacture, including one or more computer program products, having computer usable or machine readable media. The article of manufacture may be included on at least one storage media readable by a machine architecture or an image processing system embodying executable program instructions capable of performing the methodology described herein. The article of manufacture may be included as part of an operating system and may be shipped, sold, leased, or otherwise provided separately, either alone or as part of an add-on, update, upgrade, or product suite.

It will be appreciated that various of the above-disclosed and other features and functions, or alternatives thereof, may be desirably combined into many other different systems or applications. Various presently unforeseen or unanticipated alternatives, modifications, variations, or improvements therein may become apparent and/or subsequently made by those skilled in the art, which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for determining an arterial pulse transit time between a proximal and distal region of a subject of interest from source video images acquired using a video imaging system, the method comprising:

receiving time-varying source images acquired over at least one channel of a video imaging system, said source images comprising video images captured of a proximal and distal region of an area of exposed skin of a subject of interest in which plethysmographic signals can be registered and at least one background region in which plethysmographic signals cannot be registered, and said proximal and distal regions and said background region being exposed to the same environmental factors;

extracting, from said source images a first time-series signal for said proximal region and a second times series signal for said distal region and at least one background region time-series signal;

subtracting said first time-series signal and said background region times-series signal to obtain environmentally compensated time-series signal for said proximal region;

subtracting said second time-series signal and said background region times-series signal to obtain environmentally compensated time-series signal for said distal region;

computing a first phase angle $\phi_1(\omega)$ with respect to frequency $\omega$ of said environmentally compensated time-series signal for said proximal region;

computing a second phase angle $\phi_2(\omega)$ with respect to frequency $\omega$ of said environmentally compensated time-series signal for said distal region;

plotting said computed phases with respect to frequency to obtain respective phase vs frequency curves for each of said proximal and distal regions;

computing respective slopes $T_1 = \partial \phi_1 / \partial \omega$ and $T_2 = \partial \phi_2 / \partial \omega$ within a defined cardiac frequency range between 0.75 to 4.0 Hz from each of said respective phase vs frequency curves;

computing a difference between said slopes $T_1$ and $T_2$, said difference comprising an arterial pulse transit time for said subject between said proximal and distal regions; and storing, using a processor, said arterial pulse transit time to a storage device.

2. The method of claim 1, wherein said time-varying source signal comprises any combination of: NIR images, RGB images, RGB with NIR images, multispectral images, thermal images, and hyperspectral images.

3. The method of claim 1, further comprising determining, from said arterial pulse transit time, any of: a blood pressure in said subject's vascular network, a blood vessel dilation over time, a blood vessel blockage, a blood flow velocity, and the existence of a peripheral neuropathy.

4. The method of claim 1, further comprising:
processing said video images to determine a region of skin; and
isolating said proximal and distal regions from said skin regions.

5. The method of claim 1, wherein said video images are acquired by a single NIR channel, further comprising:
partitioning frames from said channel for each region into a non-skin region and a skin region; and
performing source separation to obtain both a heart rate signal and said phase vs frequency curve.

6. The method of claim 1, wherein, in advance of extracting said time-series signals, further comprising compensating for any of: a motion induced blur, an imaging blur, harmonics which are not related to components of said subject's cardiac pulse, and slow illuminant variation.

7. The method of claim 1, wherein said video imaging system used to acquire said time-varying source images of said proximal and distal regions comprises two video cameras, a first video camera acquiring a first video of said proximal region and a second video camera acquiring a second video of said distal region.

8. The method of claim 7, wherein, in advance of extracting said time-series signals, further comprising synchronizing said first and second videos with respect to time.

9. The method of claim 1, wherein the video imaging system is used in a non-contact, remote sensing environment.

10. A video based system for determining an arterial pulse transit time between a proximal and distal region of a subject of interest from source video images acquired using a video camera, the system comprising:
a video imaging system for capturing a time-varying source images over at least one channel, said source images comprising video images captured of a proximal and distal region of an exposed area of skin of a subject of interest where an arterial pulse transit time is desired to be determined; and
a processor in communication with said video camera and a memory, said processor executing machine readable instructions for performing:
receiving time-varying source images acquired over at least one channel of a video imaging system, said source images comprising video images captured of a proximal and distal region of an area of exposed skin of a subject of interest in which plethysmographic signals can be registered and at least one background region in which plethysmographic signals cannot be registered, and said proximal and distal regions and said background region being exposed to the same environmental factors;
extracting, from said source images a first time-series signal for said proximal region and a second times series signal for said distal region and at least one background region time-series signal;
subtracting said first time-series signal and said background region times-series signal to obtain environmentally compensated time-series signal for said proximal region;
subtracting said second time-series signal and said background region times-series signal to obtain environmentally compensated time-series signal for said distal region;
computing a first phase angle $\phi_1(\omega)$ with respect to frequency $\omega$ of said environmentally compensated time-series signal for said proximal region;
computing a second phase angle $\phi_2(\omega)$ with respect to frequency $\omega$ of said environmentally compensated time-series signal for said distal region;
plotting said computed phases with respect to frequency to obtain respective phase vs frequency curves for each of said proximal and distal regions;
computing respective slopes $T_1=\partial\phi_1/\partial\omega$ and $T_2=\partial\phi_2/\partial\omega$ within a defined cardiac frequency range between 0.75 to 4.0 Hz from each of said respective phase vs frequency curves;
computing a difference between said slopes $T_1$ and $T_2$, said difference comprising an arterial pulse transit time for said subject between said proximal and distal regions; and
storing, using a processor, said arterial pulse transit time to a storage device.

11. The system of claim 10, wherein said time-varying source signal comprises any combination of: NIR images, RGB images, RGB with NIR images, multispectral images, thermal images, and hyperspectral images.

12. The system of claim 10, further comprising determining, from said arterial pulse transit time, any of: a blood pressure in said subject's vascular network, a blood vessel dilation over time, a blood vessel blockage, a blood flow velocity, and the existence of a peripheral neuropathy.

13. The system of claim 10, further comprising:
processing said video images to determine a region of skin; and
isolating said proximal and distal regions from said skin regions.

14. The system of claim 10, wherein said video images are acquired by a single NIR channel, further comprising:
partitioning frames from said channel for each region into a non-skin region and a skin region; and
performing source separation to obtain both a heart rate signal and said phase vs frequency curve.

15. The system of claim 10, wherein, in advance of extracting said time-series signals, further comprising compensating for any of: a motion induced blur, an imaging blur, harmonics which are not related to components of said subject's cardiac pulse, and slow illuminant variation.

16. The system of claim 10, wherein said video imaging system used to acquire said time-varying source images of said proximal and distal regions comprises two video cameras, a first video camera acquiring a first video of said proximal region and a second video camera acquiring a second video of said distal region.

17. The system of claim 16, wherein, in advance of extracting said time-series signals, further comprising synchronizing said first and second videos with respect to time.

18. The system of claim 10, wherein the video imaging system is used in a non-contact, remote sensing environment.

19. The method of claim 1, wherein said time-varying source is a single color channel.

20. The method of claim 19, wherein said single color channel is a green color channel.

21. The method of claim 1, wherein said computing said respective slopes includes fitting a polynomial equation to each of said phase vs frequency curves.

22. The method of claim 1, wherein said computing said respective slopes includes computing a derivative with respect to frequency.

23. The system of claim 10, wherein said time-varying source is a single color channel.

24. The system of claim 23, wherein said single color channel is a green color channel.

25. The system of claim 10, wherein said computing said respective slopes includes fitting a polynomial equation to each of said phase vs frequency curves.

26. The system of claim 10, wherein said computing said respective slopes includes computing a derivative with respect to frequency.

* * * * *